US00PP26744P3

(12) United States Plant Patent
Braunig

(10) Patent No.: US PP26,744 P3
(45) Date of Patent: May 17, 2016

(54) ***SALVIA* PLANT NAMED 'FLORSALVIOBLU'**

(50) Latin Name: *Salvia nemerosa*
Varietal Denomination: Florsalvioblu

(71) Applicant: Tobias Braunig, Quedlinburg (DE)

(72) Inventor: Tobias Braunig, Quedlinburg (DE)

(73) Assignee: Florensis B.V. (NL)

( * ) Notice: Subject to any disclaimer, the term of this patent is extended or adjusted under 35 U.S.C. 154(b) by 165 days.

(21) Appl. No.: 14/120,815

(22) Filed: Jun. 30, 2014

(65) Prior Publication Data

US 2015/0382529 P1 Dec. 31, 2015

(51) Int. Cl.
*A01H 5/02* (2006.01)

(52) U.S. Cl.
USPC ..... Plt./475

(58) Field of Classification Search
USPC ..... Plt./475
See application file for complete search history.

*Primary Examiner* — Annette Para
(74) *Attorney, Agent, or Firm* — Cassandra Bright

(57) ABSTRACT

A new and distinct *Salvia* cultivar named 'Florsalvioblu' is disclosed, characterized by a compact plant form, early flowering and abundant violet colored flowers. The new variety is a *Salvia nemerosa*, normally produced as an outdoor garden or container plant.

2 Drawing Sheets

Latin name of the genus and species: *Salvia nemerosa.*
Variety denomination: 'FlorsalVioblu'.

BACKGROUND OF THE INVENTION

The new *Salvia* cultivar is a product of a planned breeding program conducted by the Inventor, Tobias Bräunig, in Quedlinburg, Germany. The objective of the breeding program was to produce new *Salvia* varieties with denser plant habits, strong garden performance, in a range of flower colors. The open pollination resulting in this new variety was made during Summer of 2010.

The seed parent is an unpatented, proprietary, *Salvia nemerosa*. The pollen parent is unknown as it was an open pollination breeding program. The new variety was identified as a potentially interesting selection in Summer 2011, at a greenhouse in Quedlinburg, Germany.

Asexual reproduction of the new cultivar 'FlorsalVioblu' by vegetative cuttings was first performed during 2011, at a research greenhouse in Quedlinburg, Germany. Subsequent propagation has shown that the unique features of this cultivar are stable and reproduced true to type on successive generations.

SUMMARY OF THE INVENTION

The cultivar 'Florsalvioblu' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Florsalvioblu' These characteristics in combination distinguish 'Florsalvioblu' as a new and distinct *Salvia* cultivar:

1. Violet flower color.
2. Compact plant form.

3. Abundant flowering.
4. Early flowering.

PARENT COMPARISON

Plants of the new cultivar 'Florsalvioblu' are similar to plants of the seed parent in most horticultural characteristics, however, plants of the new cultivar 'Florsalvioblu' differ in the following:

1. Violet flower color. The seed parent has a dark rose colored flower.
2. Less compact in plant form.
3. Earlier flowering.
4. More abundant flowering.

COMMERCIAL COMPARISON

Plants of the new cultivar 'Florsalvioblu' can also be compared to the commercial variety *Salvia* 'Mainacht", unpatented. These varieties are similar in most horticultural characteristics; however 'Florsalvioblu' differs in the following:

1. More compact plants.
2. More inflorescences.
3. Deeper violet blue color.
4. Longer flowering time.

BRIEF DESCRIPTION OF THE PHOTOGRAPHS

Figure 1:
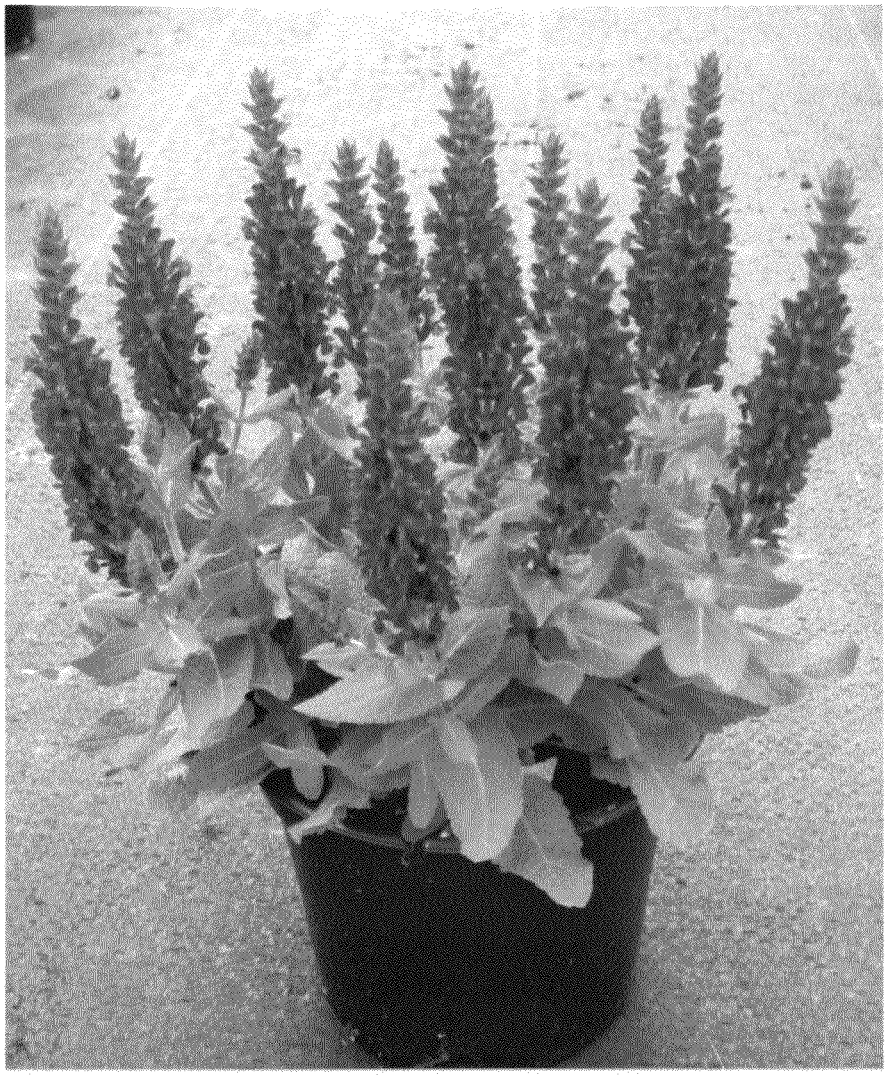

The accompanying photograph in FIG. 1 illustrates in full color a typical plant of 'Florsalvioblu' grown in a greenhouse, in Santa Paula, Calif., in a commercial 8 inch container.

Figure 2:
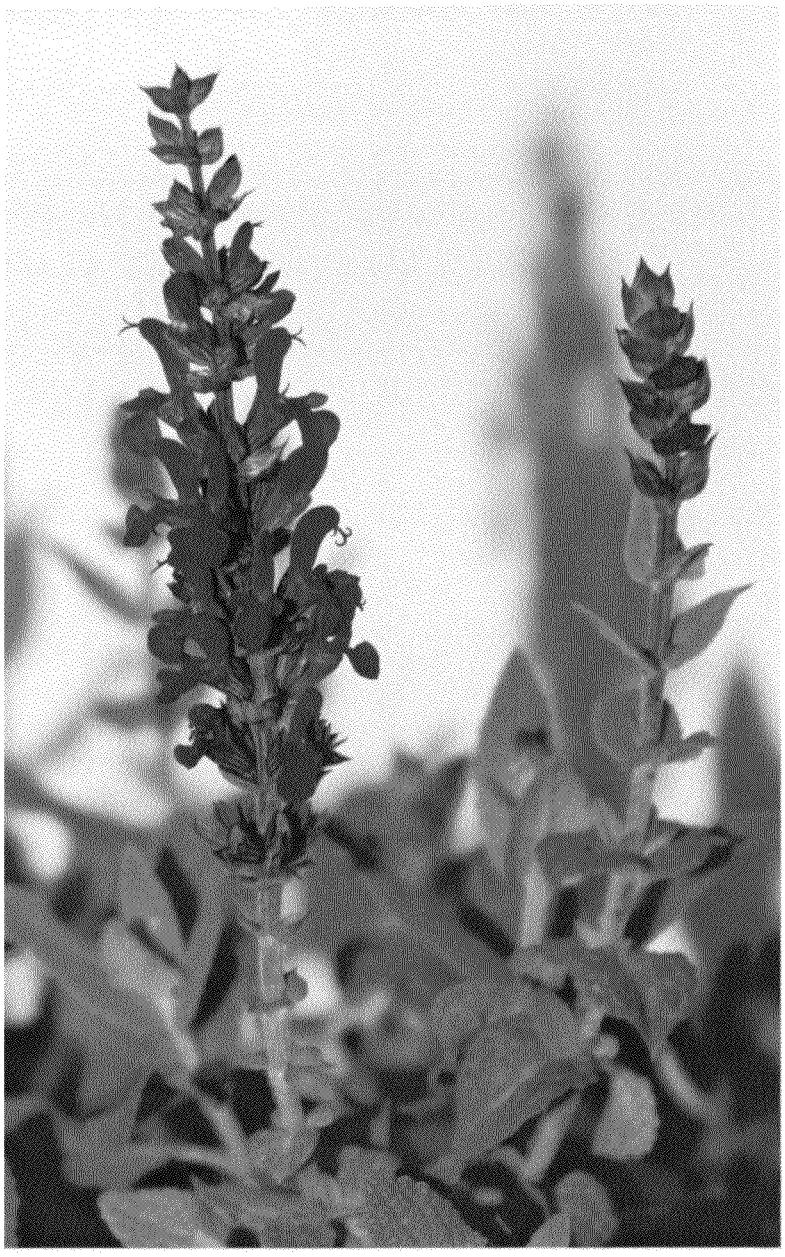

FIG. 2 illustrates in full color a typical flowers of 'Florsalvioblu'. Age of the plant photographed is approximately 16 weeks from an unrooted cutting.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'Florsalvioblu' plants grown in a greenhouse in Santa Paula, Calif. The growing temperature ranged from approximately 10° C. to 30° C. The greenhouse is un-shaded, giving bright, normal sunlight conditions. Measurements and numerical values represent averages of typical plant types.

Botanical classification: *Salvia nemerosa* 'Florsalvioblu'.

PROPAGATION

Root description: Fine, densely fibrous. Colors include Green-White 157D on new growth and Orange-White 159C, Grey-Brown 199B and 199C for older roots.

PLANT

Growth habit: Upright perennial.

Pot size of plant described: 1 gallon pot.

Height: Approximately 16 cm to top of foliage. Approximately 24 cm to top of flowering plane. Measured from soil level of pot.

Plant spread: Approximately 29 cm.

Growth rate: Rapid.

Branching characteristics: Moderately well branched. Approximately 6 to 8 primary branches per plant.

Length of primary lateral branches: Approximately 12 cm.

Diameter of lateral branches: Approximately 0.4 cm.

Quantity of lateral branches: About 18 to 24.

Stem:

*Color*.—Near RHS Green 138A.

*Texture*.—Pubescent and ribbed.

Internode length: Average 4.5 cm.

Age of plant described: Approximately 20 weeks from 3 rooted cuttings.

FOLIAGE

Leaf:

*Arrangement*.—Opposite.

*Quantity*.—Approximately 10 fully expanded per main branch.

*Average length*.—Approximately 5.0 cm. including petiole.

*Average width*.—Approximately 1.8 cm.

*Shape of blade*.—Oblong.

*Apex*.—Acute.

*Base*.—Truncate.

*Attachment*.—Stalked.

*Margin*.—Minutely dentate.

*Texture of top surface*.—Matte, glabrous. Shallowly reticulate.

*Texture of bottom surface*.—Matte, glabrous, reticulate.

*Color*.—Young foliage upper side: Near RHS Green 137C. Young foliage under side: Near RHS Green 137D. Mature foliage upper side: Near RHS Green 137A. Mature foliage under side: Near RHS Green 138A.

*Venation*.—Type: Reticulate. Venation color upper side: Near RHS Green 138B. Venation color under side: Near RHS Green 138C.

*Petiole*.—Average Length: Approximately 0.3 cm. Diameter: Approximately 0.2 cm. Color: Near Green 138B.

FLOWER

Natural flowering season: Flowering from early Spring through late Summer.

Inflorescence type and habit: Flowers arranged in verticillasters on spikes.

Flower longevity on plant: Individual flowers last approximately 2 to 3 days on the plant. Each spike lasts approximately 4 weeks with flowers.

Quantity of flowers: About 16 buds and 16 fully opened flowers per spike, at one time. Mature plants have approximately 18 to 24 spikes.

Spike size: Diameter: Approximately 2.0 cm. Height: Approximately 8.0 cm.

Individual flowers:

*Size*.—Diameter: Approximately 0.8 cm. Length: Approximately 1.2 cm.

*Persistence*.—Non-persistent.

*Fragrance*.—Faint.

Corolla:

*Petal arrangement*.—The corolla is sympetalous and typically bilabiate with 2 small, fully fused lobes forming a single upper lip and 3 larger fused lobes forming a lower lip.

*Margin*.—Entire.

*Tip shape*.—Upper lip tip obtuse, lower lip tip recuse.

*Length*.—Upper lip Approximately 0.6 cm. Lower lip Approximately 0.35 cm. Tube length Approximately 0.6 cm.

*Width*.—Upper lip: Approximately 0.2 cm, lower lip Approximately 0.4 cm. Tube width: Approximately 0.25 cm.

*Texture*.—Upper lip: Glabrous all surfaces. Lower lip: Glabrous all surfaces.

Color:

*Upper lip*.—When opening: Inner surface: Near RHS Violet N88B. Outer surface: Near RHS Violet N88A. Fully opened: Inner surface: Near RHS Violet 86A. Outer Surface: Near RHS Violet N88A. Fading: Inner surface: Near RHS Violet-Blue N92B. Outer surface: Near RHS Violet-Blue N92B.

Color:

*Lower lip*.—When opening: Inner surface: Near RHS Violet-Blue N89A. Outer surface: Near RHS Violet-Blue N89B. Fully opened: Inner surface: Near RHS Violet-Blue N88A. Outer surface: Near RHS Violet-Blue N88B. Fading: Inner surface: Near RHS Violet-Blue N92B. Outer surface: Near RHS Violet-Blue N92B.

Color:

*Tube*.—When opening: Inner surface: Near RHS Violet 84D. Outer surface: Violet 83D, base near Violet 85D. Fully opened: Inner surface: Near RHS Violet 84D. Outer surface: Violet 83D, base near Violet 85D. Fading: Inner surface: Near RHS Violet-Blue 93C. Outer surface: Near RHS Violet 83D.

Bud:

*Shape*.—Ovoid.

*Length*.—Approximately 0.6 cm.

*Diameter*.—Approximately 0.3 cm.

*Color*.—Near RHS Violet-Blue N89A.

Calyx:
*Length*.—Approximately 0.4 cm.
*Diameter*.—Approximately 0.3 cm.
*Shape*.—Tubular.
Sepals:
*Shape*.—Quantity per flower: 3, fused to form a tube. Unfused apex.
*Length*.—Approximately 0.4 cm.
*Width*.—Approximately 0.2 cm.
*Margin*.—Entire.
*Apex*.—Acute.
*Texture*.—Softly pubescent.
*Color*.—Immature: Near RHS Purple N79B, base green 137B. Mature: Near RHS Purple N79B, base green 137B.
Peduncle:
*Length*.—Average 2.0 cm.
*Diameter*.—0.3 cm.
*Color*.—Near RHS Green 137C.
*Orientation*.—Upright, straight.
*Strength*.—Strong.
*Texture*.—Softly pubescent, ridged.
Pedicels:
*Length*.—Average 0.1 cm.
*Diameter*.—0.1 cm.
*Color*.—Near RHS Purple N79B.
*Orientation*.—Straight, approximately 45 degree angle from attachment.
*Strength*.—Flexible.
*Texture*.—Pubescent.

REPRODUCTIVE ORGANS

Stamens:
*Number*.—2.
*Filament length*.—Approximately 0.6, approximately 0.3 cm of length fused to petal.
*Filament color*.—Near RHS Violet 84B.
Anthers:
*Shape*.—Very narrowly elliptic.
*Length*.—Approximately 1.5 mm.
*Color*.—Near RHS Purple N79B.
*Pollen*.—Pollen production not observed.
Pistil:
*Number*.—1.
*Length*.—Approximately 0.8 cm.
*Style*.—Length: Approximately 0.7 cm. Color: Near Violet N87C.
*Stigma*.—Shape: Forked. Color: Near RHS Violet 83A. Ovary color: Near RHS Green 137B.

OTHER CHARACTERISTICS

Seeds and fruits: Not observed to date.
Disease/pest resistance: Neither resistance nor susceptibility to pathogens and pests common to *Salvia nemerosa* have been observed.
Temperature tolerance: The new variety tolerates temperatures within USDA zones 3 to 8.

What is claimed is:

1. A new and distinct cultivar of *Salvia* plant named 'FLORSALVIOBLU' as herein illustrated and described.

* * * * *